US010912668B2

(12) United States Patent
Logier et al.

(10) Patent No.: US 10,912,668 B2
(45) Date of Patent: Feb. 9, 2021

(54) DEVICE ALLOWING AN ALIMENTARY BOLUS FLOW BETWEEN TWO STOMAS

(71) Applicant: CENTRE HOSPITALIER REGIONAL UNIVERSITAIRE DE LILLE, Lille (FR)

(72) Inventors: Régis Logier, Marquette-les-Lille (FR); Jean-Pierre Sozanski, Villeneuve d'Ascq (FR); Jean-Robert Nzamush Elepan Mabla, Braines l'Alleud (BE)

(73) Assignee: CENTRE HOSPITALIER REGIONAL UNIVERSITAIRE DE LILLE, Lille (FR)

( * ) Notice: Subject to any disclaimer, the term of this patent is extended or adjusted under 35 U.S.C. 154(b) by 324 days.

(21) Appl. No.: 15/781,194

(22) PCT Filed: Dec. 5, 2016

(86) PCT No.: PCT/IB2016/057348
§ 371 (c)(1),
(2) Date: Jun. 4, 2018

(87) PCT Pub. No.: WO2017/103727
PCT Pub. Date: Jun. 22, 2017

(65) Prior Publication Data
US 2018/0353318 A1    Dec. 13, 2018

(30) Foreign Application Priority Data
Dec. 15, 2015    (FR) ..................................... 15 62433

(51) Int. Cl.
*A61F 5/44*        (2006.01)
*A61F 5/445*       (2006.01)
*A61M 1/00*        (2006.01)

(52) U.S. Cl.
CPC .............. *A61F 5/4405* (2013.01); *A61F 5/44* (2013.01); *A61F 5/445* (2013.01); *A61M 1/0066* (2013.01); *A61M 2210/1042* (2013.01)

(58) Field of Classification Search
CPC .......... A61F 5/44; A61F 5/4405; A61F 5/445; A61M 1/0066; A61M 2210/1042
See application file for complete search history.

(56) References Cited

U.S. PATENT DOCUMENTS

| 2013/0197458 A1 | 8/2013 | Salama ......................... 604/335 |
| 2013/0304231 A1 | 11/2013 | Errico et al. ............... 623/23.68 |
| 2015/0351954 A1* | 12/2015 | Logier .................... A61M 1/00 604/335 |

FOREIGN PATENT DOCUMENTS

| WO | WO 2009/046995 A1 | 4/2009 |
| WO | WO 2014/122378 A1 | 8/2014 |

OTHER PUBLICATIONS

International Search Report dated Mar. 15, 2017 in corresponding PCT International Application No. PCT/IB2016/057348.
(Continued)

*Primary Examiner* — Kai H Weng
(74) *Attorney, Agent, or Firm* — Ostrolenk Faber LLP

(57) ABSTRACT

A device allowing the creation of an alimentary bolus flow between two stomas, including means forming a pump; first/second sealed connection means capable of connecting the suction opening to an upstream/downstream stoma located on the abdominal wall of a patient; and first and/or second anti-reflux means. The first and/or second anti-reflux means includes a cavity into which the alimentary bolus passes, an inflatable balloon mounted in the cavity and means for inflating the balloon, that make it possible to modify the inflation of the latter, and the balloon is shaped to shift from an open position in which the balloon is partially inflated and has a neck allowing the passage of the (Continued)

alimentary bolus, to a closed position in which the balloon is more inflated than in the open position and in which the balloon is in contact with the wall of the cavity and the neck is sealed as a result of the portion of the wall of the balloon defining the neck being compressed against itself, at least over a portion of the height of the neck.

7 Claims, 3 Drawing Sheets

(56) References Cited

OTHER PUBLICATIONS

Written Opinion dated Mar. 15, 2017 in corresponding PCT International Application No. PCT/IB2016/057348.

* cited by examiner

DEVICE ALLOWING AN ALIMENTARY BOLUS FLOW BETWEEN TWO STOMAS

CROSS-REFERENCE TO RELATED APPLICATIONS

The present application is a 35 U.S.C. §§ 371 national phase conversion of PCT/IB2016/057348, filed Dec. 5, 2016, which claims priority to French Patent Application No. 15/62433, filed Dec. 15, 2015, the contents of which are incorporated herein by reference. The PCT International Application was published in the French language.

TECHNICAL FIELD

The present application concerns a device enabling an alimentary bolus flow between two stomas of the type including anti-flowback means comprising a balloon having a neck for the passage of the alimentary bolus.

BACKGROUND OF THE INVENTION

Document WO 2014/122378 describes a device for circulating an alimentary bolus flow between two stomas. This device includes a suction duct and a discharge duct. The alimentary bolus is ejected naturally from a first stoma toward the manifold of the aforementioned device. The suction duct allows the suction of the alimentary bolus contained in the manifold toward the suction duct of the device. This allows, in turn, discharging the sucked alimentary bolus into the second intestine portion at the level of the second stoma. In the aforementioned document, the suction and discharge ducts are each equipped with a check valve. This check valve can be of the duckbill type that is to say formed of two flexible lips likely to move away from each other in order to let an alimentary bolus flow pass in one direction. The check valves can also be simple flaps movably mounted in the considered duct so as to allow the passage of the alimentary bolus in one direction.

The two types of check valve or anti-flowback means mentioned above have proved not to be adapted to the alimentary bolus. Indeed, the latter contains solid pieces that are likely to get jammed between the two lips of the duckbill-type valve. Similarly, these solid pieces often remain jammed between the flap and the wall of the duct preventing the change of position of the flap and clogging partially the duct itself.

Moreover, the sealing of the two aforementioned check valves is not satisfactory. Poor sealing can even prevent any pumping from the alimentary bolus or even generate an alimentary bolus flow in the direction opposite to the desired one.

SUMMARY OF THE INVENTION

An object of the present invention is to find a solution of at least one of aforementioned problems.

The present invention thus proposes a device allowing to create an alimentary bolus flow between two stomas, of the type including:

pump-forming means which have a suction opening and a discharge opening, which are adapted to suck an alimentary bolus through said suction opening and discharge it through said discharge opening, said pump-forming means being external to the patient's body and capable of being mounted on the body of a patient, first sealed connection means capable of linking said suction opening to an upstream stoma, located on the abdominal wall of a patient;

second sealed connection means capable of linking said discharge opening to a downstream stoma, disposed on the abdominal wall of said patient; and first and/or second anti-flowback means capable of avoiding the flowback of the alimentary bolus sucked or discharged by said means forming a pump toward said suction and/or discharge opening.

According to the invention, typically, said first and/or second anti-flowback means include:

a cavity in which said alimentary bolus transits;

an inflatable balloon mounted in said cavity; and means for inflating said balloon which allow modifying the inflation of the latter, said balloon is shaped to move from an open position in which said balloon is partially inflated and has a neck that allows the passage of the alimentary bolus, to a closed position in which said balloon is more inflated than in said open position and in which said balloon is in contact with the wall of said cavity and said neck is obturated, in particular due to the crushing of the wall portion of said balloon defining said neck on itself, on at least one portion of the height of said neck.

The neck of the balloon allows forming a passage wider than that of the duckbill-type valves. The inflation and deflation of the balloon allow easily controlling the size of the neck and therefore the alimentary bolus flow.

The obturation of the neck is obtained by the narrowing of the latter and then by contact of the wall portion of the balloon defining said neck with itself, on at least one portion of the height of the neck.

The balloon can also be easily used for the detection of the presence of alimentary bolus in the device of the invention.

The mounting of the balloon in the cavity is not limited according to the invention. Thus, when the balloon is in the open position, the alimentary bolus can pass through the neck only or through the neck and between the wall of the cavity and the balloon.

Advantageously, said balloon is mounted in said cavity so as, in said open position, the wall of said balloon remains in contact with the wall of said cavity, whereby the alimentary bolus circulates only through said neck. A large-size passage for the transit of the alimentary bolus is thus released; the neck formed by the balloon thus reaches its maximum size in the open position and there is no risk for the balloon to be ripped at the passage of the alimentary bolus.

The shape of the balloon is not limited according to the invention as soon as it has a neck that can be deformed to shut by contact when the balloon exceeds a given inflation state. The balloon can be substantially cylindrical with a substantially cylindrical and central passage that defines the neck. It can also be substantially annular or substantially toroidal (donut shaped).

According to the invention, the shape of the cavity and/or the shape of the balloon are not limited. The cavity can have substantially the same section as said suction or discharge duct and be a portion of said suction or discharge duct. The cavity can have a section of a dimension equal to or greater than the section of said suction or discharge duct. The cavity may have a circular or elliptical section in a plane perpendicular to the length of the duct and/or in a plane parallel to the length of the considered duct.

The balloon can be mounted in the cavity by means of a support or directly on the wall of said cavity. It can be sticked on the wall of the cavity, for example. The balloon can be mounted directly or indirectly on said wall of said cavity. The balloon is thus formed in the cavity, which prevents the passage of the alimentary bolus between the wall of the cavity and the balloon, even in the open position.

According to a preferred embodiment, the anti-flowback means include, in addition, a ring which includes said cavity and a strip made of elastically deformable material sealingly fixed on the wall of said cavity and forming said inflatable balloon. This ring can be sealingly mounted in the discharge/suction duct.

According to another embodiment, the balloon may have a toroidal shape and its outer surface is stuck on the ring, inside the cavity.

According to another embodiment, the balloon is cylindrical, and its two ends are linked to each other; it thus forms a crown or torus.

Advantageously, said ring includes a perforation for the passage of a fluid coming from said balloon inflation means and a groove recessed within the thickness of the wall of said ring and which opens at the level of said perforation. The groove allows preventing the membrane forming the balloon from sticking against the wall of the cavity in the open position or even from being sucked by the means forming a pump. This groove allows the passage of the fluid (air or other gas, or even liquid) coming from means forming un pump and its distribution throughout the volume of the balloon.

Advantageously, said first and/or second anti-flowback means are part of said first sealed connection means and/or said second sealed connection means.

Advantageously, said cavity and said balloon are conformed in order that in said open position, said balloon contacts the wall of said cavity.

According to a particular embodiment of the means forming a pump, which is not necessarily combined with the aforementioned anti-flowback means, these include a deformable membrane forming a cup, said membrane is capable of reversibly moving from a first position in which the first face of said membrane forms the concave inner surface of said cup to a second position in which said first face forms the convex outer surface of said cup.

The device can also include means for detecting the presence of alimentary bolus in said first collection means and in particular means for detecting the presence of alimentary bolus that include means for detecting an overpressure in the balloon equipping said first anti-flowback means.

According to the invention, the device may comprise two balloons, each connected to inflation means of its own.

The shape and size of the balloon are not limitative of the invention.

BRIEF DESCRIPTION OF THE DRAWINGS

The present invention, its features and the various advantages it provides will appear more clearly upon reading the following detailed description of an embodiment, presented as an illustrative and not limiting example, with reference to the appended figures in which.

DESCRIPTION OF PREFERRED EMBODIMENTS

Figure 1:
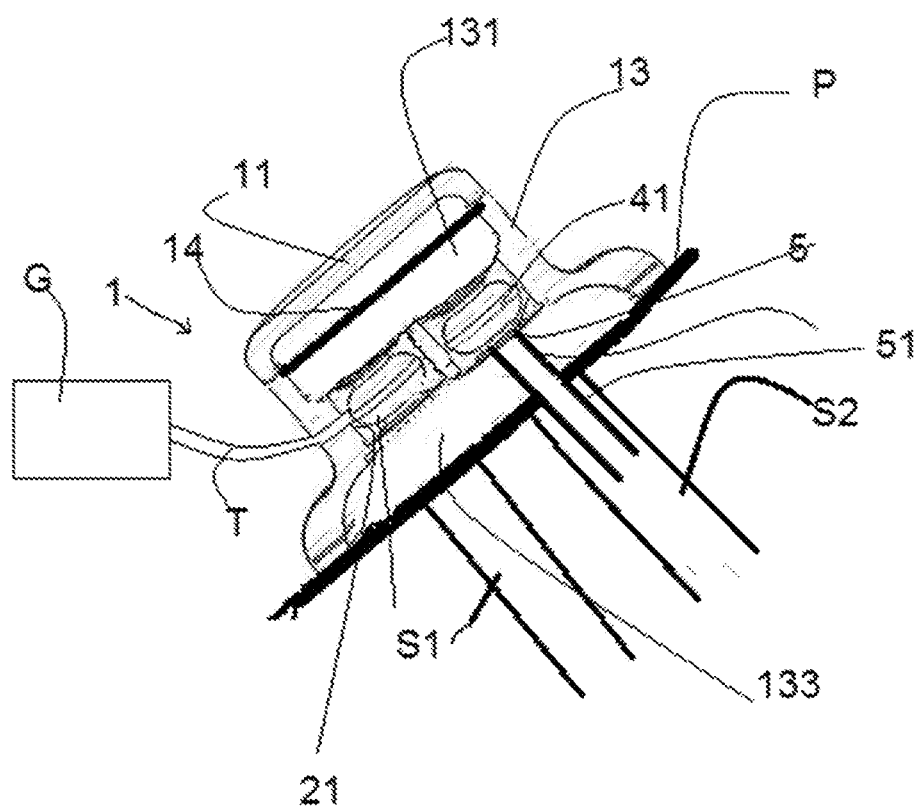
FIG. 1 represents a cross-sectional view of a particular embodiment of the first and second sealed connection means, these being mounted on the abdomen of a patient that has two stomas.

With reference to FIG. 1, the device includes a single manifold 1 which constitutes the first and second sealed connection means to the upstream and downstream stomas S1 and S2 which are performed on the patient's abdomen. This device is adapted for close ostomies that can be covered by a single manifold. The manifold 1 includes a cover 11 fixed on a manifold body 13. The manifold body 13 has a membrane housing 131 which contains a membrane 14. A suction duct 3 and a discharge duct 5 are arranged in the manifold body 13 and open into the membrane housing 131. The manifold body 13 also comprises a collection housing 133 into which also open the suction 3 and discharge 5 ducts. The membrane housing 131 and the collection housing 133 are linked to each other by the suction 3 and discharge 5 ducts. The collection housing 133 is fixed on the skin P of the patient's abdomen, above the two stomas S1 and S2. The discharge duct 5 comprises a nozzle which passes through the collection housing 133 and on which a tube 51 is connected. This tube 51 is inserted in an open intestine portion at the level of the downstream stoma S2. The suction duct 3 opens directly into the collection housing 133. The suction duct 3 comprises first anti-flowback means 33 while the discharge duct comprises second anti-flowback means 53 which will be both described in more detail with reference to FIGS. 2 to 4. The two ducts 3 and 5 do not communicate directly with each other and are arranged in the manifold body 13, between the membrane housing 131 and the collection housing 133. The cavity 21 is arranged in the suction duct, while the cavity 41 is arranged in the discharge duct. These two cavities 21 and 41 are substantially identical and each have an ellipsoidal section in a plane perpendicular to the ducts 3 and 5; the longest dimension is perpendicular to the ducts 3 and 5, respectively. The two cavities 21 and 41 are formed in cylindrical rings 2 sealingly mounted in the ducts 3 and 5, as more fully explained with reference to FIG. 2. Means G for inflating the balloons of the first and second anti-flowback means include inflation tubes T that are connected to these balloons. In FIG. 1, the balloons are not represented for the sake of clarity and only one tube T has been represented.

Figure 2:
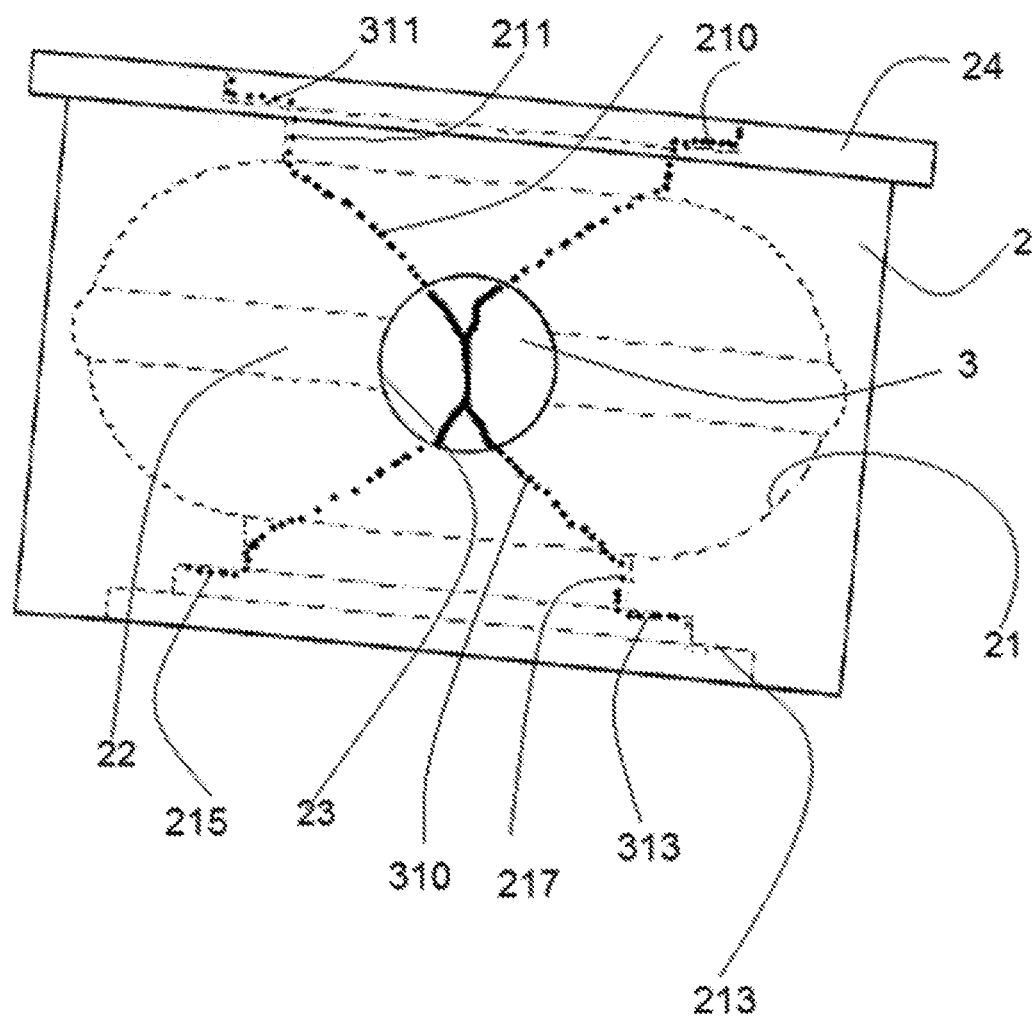
FIG. 2 represents schematically a front view of a particular embodiment of the anti-flowback means of the invention.

FIG. 2 represents in more detail an embodiment of the first anti-flowback means. In the particular embodiment represented herein, the first and second anti-flowback means are identical, but the invention is not limited to this embodiment.

With reference to FIG. 2, the anti-flowback means include a ring 2 with a substantially tubular outer surface and capable of being sealingly mounted in the suction duct 3 or in the discharge duct 5 of the manifold 1. This ring 2 includes an inner cavity 21 of substantially circular maximum section. The cavity 21 has an ellipsoidal shape substantially similar to that of a rugby balloon. A groove 22 is arranged over the whole section of the cavity 21. The cavity 21 has a perforation 23 on which is fixed the end of the tube T (see FIG. 1) which is connected to the inflation means and thus allows inflating more or less the balloon. The groove 22 opens at the perforation 23.

The ring 2 has a shoulder 24 which bears on the surface of the collection body 13 at the mouth of the suction 3 or discharge 5 duct, in the membrane chamber 131. The cavity 21 is open upwardly and downwardly of the ring 2. A first counterbore 210 is performed at the upper end of the ring 2, which comprises the shoulder 24. This counterbore 210 is extended by a first cylindrical passage 211 which opens into the cavity 21. Similarly, at the other end of the ring 2, there is a second counterbore 213 which is extended by a third counterbore 215 of a smaller section. This counterbore 215 is extended by a second substantially cylindrical passage 217 which opens into the cavity 21. The aforementioned cavity 21, counterbores and passages form a passage for the transit of the alimentary bolus.

With reference to FIG. 2, the balloon 3 is formed by a cylindrical strip 310 made of elastically deformable material and usable in the medical field for a prolonged contact with the human body. The strip 310 presents a high edge 311 which is fixed by gluing on the vertical portion of the passage 211 and on the horizontal portion of the first counterbore 210, along the entire perimeter of their section. The lower edge 313 of the strip 310 is fixed by gluing on the horizontal portion of the third counterbore 215 and on the vertical wall of the second passage 217.

In FIG. 2, the balloon 3 formed by the strip 310 is in the closed position. It is inflated by the inflation means G and the opposite strip portions 310 according to a diameter of the section of the cavity 21 are in contact on a portion of the height of the strip 310. The neck 32 is crushed, tightened on itself according to the diameter of the cavity 21 (i.e. the dimension substantially perpendicular to the height of the ring 2) due to the inflation of the balloon 3. The balloon 3 occupies the whole section of the cavity 21, preventing the passage of the alimentary bolus through the neck 32 which is then non-existent.

Figure 3:
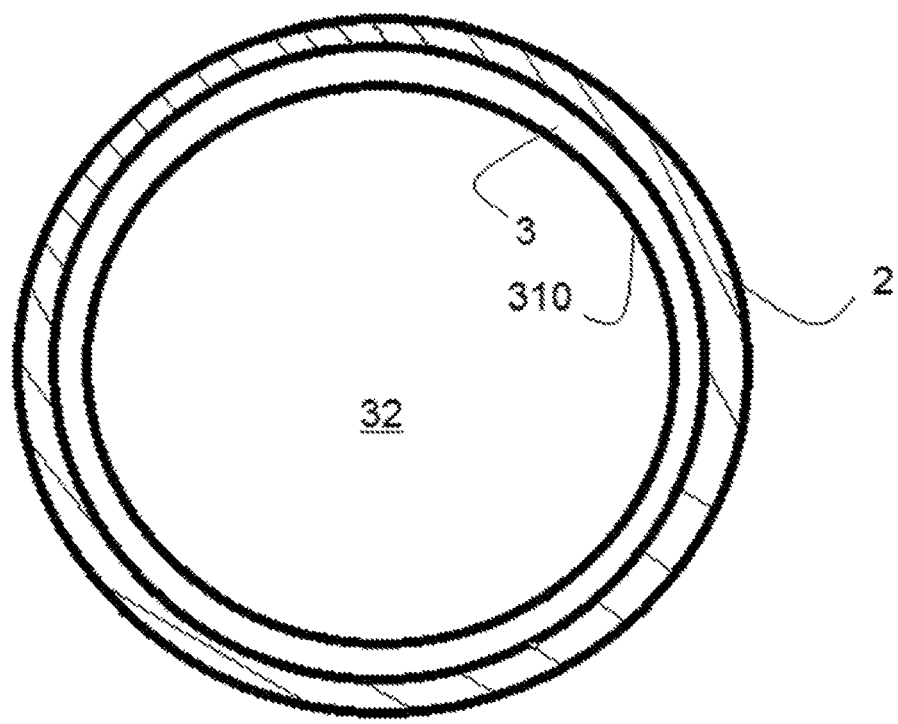
FIG. 3 represents schematically a top view of the anti-flowback means represented in FIG. 2, the balloon being in the open position.

With reference to FIG. 3, when the balloon 3 is deflated and therefore in the open position, the strip 310 is close to the wall of the cavity 21 and forms a torus whose neck 32 (or opening) allows the passage of the alimentary bolus. It is even possible by modulating the inflation of the balloon to stick the membrane 310 against the wall of the cavity 21, under the effect of the suction generated by the inflation means G. The cavity is therefore free and allows the passage of the alimentary bolus.

Figure 4:
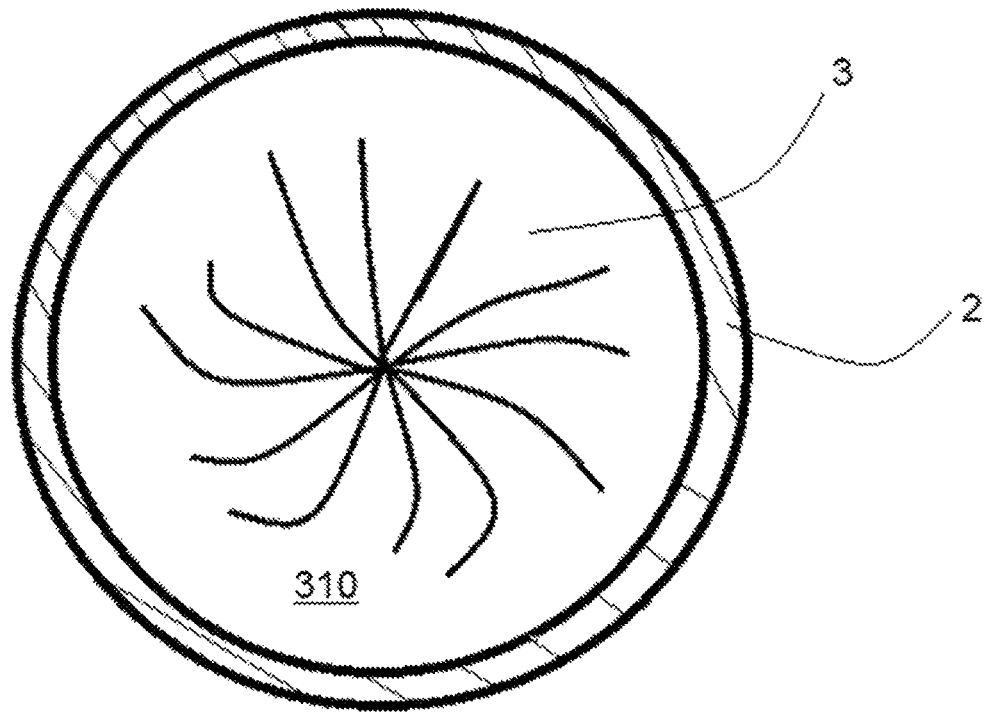
FIG. 4 represents a top view of the anti-flowback means represented in FIG. 2, the balloon being in the closed position.

With reference to FIG. 4, it will be noted that, when the balloon is inflated, there is no more passage for the alimentary bolus, the neck 32 no longer exists and has crushed on itself. The strip 310 comes into contact with itself and due to the fluid pressure existing in the balloon 3 ensures a sealed closure of the neck 32; the alimentary bolus can no longer pass through the cavity 21.

The operation of the device of the invention will be explained in more detail with reference to FIGS. 1 to 4.

When the alimentary bolus arrives in the intestine, upstream of the upstream stoma S1, it is ejected due to the intestinal contractions in the suction duct 3. It crosses the cavity 21 through the neck 32 of the balloon 3 and reaches the membrane chamber 131. The inflation means G inflate the balloon 3 located in the suction duct so as to obturate the neck 32. The means forming a pump expel the alimentary bolus due to the deformation of the membrane 14 toward the discharge duct 5, the balloon 3 equipping the discharge duct being deflated and therefore in the open position. The alimentary bolus thus crosses the cavity 41 and the discharge tube 5; it then penetrates the intestine portion downstream of the downstream stoma 2. The inflation means G then inflate the balloon 3 located in the cavity 41 to avoid flowback of the alimentary bolus toward the discharge duct 5 and toward the membrane chamber 131.

The opening of the balloon 3 located in the cavity 21 of the suction duct allows the rise of the alimentary bolus collected in the collection chamber 133 toward the membrane chamber 131 and the cycle starts again as previously exposed, until there is no more alimentary bolus in the collection chamber 133.

According to another embodiment, not represented, the device includes two manifolds linked by a tube. The first manifold is disposed on the upstream stoma S1 while the second one is disposed on the downstream stoma S2.

According to another embodiment, not represented, the device includes a pressure sensor mounted to measure the pressure prevailing in the balloons 3. This sensor allows detecting the presence of alimentary bolus downstream or upstream of balloon 3; indeed, the alimentary bolus pressing the balloon 3, it changes the pressure prevailing in the latter which indicates the presence of the alimentary bolus in the device according to the invention.

The invention claimed is:

1. A device allowing to create an alimentary bolus flow between two stomas, of the type including:
   pump-forming means which have a suction opening and a discharge opening, which are adapted to suck an alimentary bolus through said suction opening and discharge said alimentary bolus through said discharge opening, said pump-forming means being external to the patient's body and capable of being mounted on the body of a patient,
   a suction duct and a discharge duct comprising said suction opening and said discharge opening, respectively,
   first sealed connection means capable of linking said suction opening to an upstream stoma, located on the abdominal wall of a patient;
   second sealed connection means capable of linking said discharge opening to a downstream stoma, disposed on the abdominal wall of said patient; and
   first and/or second anti-flowback means capable of avoiding the flowback of the alimentary bolus sucked or discharged by said means forming a pump toward said suction and/or discharge opening;
   wherein said first and/or second anti-flowback means include:
   a cavity in which said alimentary bolus transits;
   an inflatable balloon mounted in said cavity; and
   means for inflating said balloon which allow modifying the inflation of the latter, and wherein said balloon is shaped to move from an open position in which said balloon is partially inflated and has a neck that allows passage of the alimentary bolus, to a closed position in which said balloon is more inflated than in said open position and in which said balloon is in contact with the wall of said cavity and said neck is obturated, due to crushing of the wall portion of said balloon defining said neck against one another, on at least one portion of the height of said neck,
   wherein said anti-flowback means include, in addition, a ring mounted in said suction duct or in said discharge duct, said ring including said cavity and a strip made of elastically deformable material sealingly fixed on the wall of said cavity and forming said inflatable balloon,
   and wherein said ring includes a perforation for the passage of a fluid coming from said balloon inflation means and a groove recessed within the thickness of the wall of said ring, arranged over the whole section of the cavity and which opens at the level of said perforation.

2. The device according to claim 1, wherein said balloon is mounted in said cavity so as, in said open position, the wall of said balloon remains in contact with the wall of said cavity, whereby the alimentary bolus circulates only through said neck.

3. The device according to claim 1, wherein said balloon is substantially toroidal.

4. The device according to claim 1, wherein said first and/or second anti-flowback means are part of said first sealed connection means and/or said second sealed connection means.

5. The device according to claim 1, wherein said cavity and said balloon are conformed in order that in said open position, said balloon contacts the wall of said cavity.

6. The device according to claim 1, wherein said means forming a pump include a deformable membrane forming a cup, said membrane is capable of reversibly moving from a first position in which the first face of said membrane forms the concave inner surface of said cup to a second position in which said first face forms the convex outer surface of said cup.

7. The device according to claim 1, wherein said device includes means for detecting the presence of alimentary bolus in said first sealed collection means and wherein said means for detecting the presence of alimentary bolus and include means for detecting an overpressure in the balloon equipping said first anti-flowback means.

\* \* \* \* \*